(12) United States Patent
Clark et al.

(10) Patent No.: US 7,253,340 B2
(45) Date of Patent: Aug. 7, 2007

(54) FLORAL ORGAN TISSUE-SPECIFIC EXPRESSION OF ISOPENTENYL TRANSFERASE

(75) Inventors: David Grayson Clark, Gainesville, FL (US); Holly Marie Loucas, Newberry, FL (US)

(73) Assignee: University of Florida Research Foundation, Gainesville, FL (US)

( * ) Notice: Subject to any disclaimer, the term of this patent is extended or adjusted under 35 U.S.C. 154(b) by 5 days.

(21) Appl. No.: 11/043,328

(22) Filed: Jan. 26, 2005

(65) Prior Publication Data

US 2005/0183159 A1 Aug. 18, 2005

Related U.S. Application Data

(60) Provisional application No. 60/540,984, filed on Feb. 2, 2004.

(51) Int. Cl.
- *C12N 15/82* (2006.01)
- *A01H 5/00* (2006.01)
- *C07H 21/04* (2006.01)

(52) U.S. Cl. ................ 800/290; 800/287; 800/288; 800/298; 800/295; 536/23.2; 536/23.7; 536/24.1; 435/320.1; 435/468; 435/419

(58) Field of Classification Search ............... 800/278, 800/287, 288, 290; 435/320.1, 468; 536/23.1, 536/23.2, 23.7, 24.1

See application file for complete search history.

(56) References Cited

U.S. PATENT DOCUMENTS

| | | | |
|---|---|---|---|
| 5,177,307 A | 1/1993 | Houck et al. | 800/205 |
| 5,424,200 A | 6/1995 | McPherson et al. | 435/70.1 |
| 5,792,934 A | 8/1998 | Smigocki et al. | 800/205 |
| 5,981,839 A | 11/1999 | Knauf et al. | 800/287 |
| 6,268,552 B1 | 7/2001 | Li | 800/317.4 |
| 6,294,714 B1 | 9/2001 | Matsunaga et al. | 800/290 |
| 6,329,570 B1 | 12/2001 | Martineau | 800/290 |
| 6,359,197 B1 | 3/2002 | Amasino et al. | 800/290 |
| 6,410,826 B1 | 6/2002 | Yanofsky et al. | 435/69.1 |
| 6,541,683 B1 | 4/2003 | Yanofsky et al. | 800/290 |
| 2003/0033639 A1 | 2/2003 | Matsunaga et al. | 800/294 |

OTHER PUBLICATIONS

Hill TA, Day CD, Zondlo SC, Thackeray AG, and Irish VF. (1998) Discrete spatial and temporal cis-acting elements regulate transcription of the Arabidopsis floral homeotic gene APETALA3. Development, vol. 125, pp. 1711-1721.*
Sa G, Mi M, He-Chun Y, and Guo-Feng L. (2002) Anther-specific expression of ipt gene in transgenic tobacco and its effect on plant development. Transgenic Research, vol. 11, pp. 269-278.*
Salisbury FB and Ross CW. (1978) Plant Physiology Second Edition. Wadsworth Pulishing Company, Inc. Belmont, California.*
Wang J, Letham DS, Cornish E, and Stevenson KR. (1997) Studies of cytokinin action and metabolism using tobacco plants expressing either the IPT or the GUS gene controlled by a chalcone synthase promoter. Aust. J. Plant Physiol. vol. 24, pp. 661-672.*
Chang H, Jones ML, Banowetz GM, and Clark DG. (2003) Overproduction of cytokinins in petunia flowers transformed with PSAG12-IPT delays corolla senescence and decreases sensitivity to ethylene. Plant Phys. vol. 132, pp. 2174-2183.*
Jones et al. Plant Systematics, 2nd Edition. McGraw-Hill, Inc., p. 245.*
Fritze et al. Developmental and UV Light Regulation of the Snapdragon Chalcone Synthase Promoter. (1991) The Plant Cell, vol. 3, pp. 893-905.*
Gen Bank Accession No. AL132971 dated Apr. 16, 2005.
Gen Bank Accession No. U30729 dated Mar. 16, 1996.
Gen Bank Accession No. AF248971 dated Oct. 4, 2001.
Gen Bank Accession No. AF248972 dated Oct. 4, 2001.
Gen Bank Accession No. AF248984 dated Oct. 4, 2001.
Gen Bank Accession No. AF248981 dated Oct. 4, 2001.
Gen Bank Accession No. AF248973 dated Oct. 4, 2001.
Gen Bank Accession No. AF248974 dated Oct. 4, 2001.
Gen Bank Accession No. AF248975 dated Oct. 4, 2001.
Gen Bank Accession No. AF248982 dated Oct. 4, 2001.
Gen Bank Accession No. AF248978 dated Oct. 4, 2001.
Gen Bank Accession No. AF043610 dated Sep. 24, 2001.
Gen Bank Accession No. AF248980 dated Oct. 4, 2001.
Gen Bank Accession No. AF248983 dated Oct. 4, 2001.
Gen Bank Accession No. AF248985 dated Oct. 4, 2001.
Gen Bank Accession No. AF248970 dated Oct. 4, 2001.
Gen Bank Accession No. AF248979 dated Oct. 4, 2001.
Gen Bank Accession No. AF248976 dated Oct. 4, 2001.
Gen Bank Accession No. AF248977 dated Oct. 4, 2001.
Gen Bank Accession No. AF248968 dated Oct. 4, 2001.
Gen Bank Accession No. AF248969 dated Oct. 4, 2001.
Gen Bank Accession No. ATU30729 dated Mar. 16, 1996.
Gen Bank Accession No. NC003308 dated Oct. 15, 2004.
Gen Bank Accession No. X14410 dated Sep. 12, 1993.
Gen Bank Accession No. BQ698482 dated May 7, 2003.
Gen Bank Accession No. BM158885 dated May 7, 2003.
Gen Bank Accession No. BG275588 dated May 7, 2003.
Gen Bank Accession No. BF609263 dated May 7, 2003.
Gen Bank Accession No. BF169921 dated May 7, 2003.
Gen Bank Accession No. AF109376 dated May 29, 2002.
Gen Bank Accession No BH012217 dated May 18, 2001.
Gen Bank Accession No. AB032122 dated Sep. 11, 1999.
Gen Bank Accession No. AJ242867 dated Apr. 15, 2005.
Gen Bank Accession No. AB025109 dated Mar. 27, 1999.
Gen Bank Accession No. M91610 dated Apr. 24, 1996.
Gen Bank Accession No. M15991 dated Apr. 27, 1993.

(Continued)

*Primary Examiner*—Ashwin D. Mehta
*Assistant Examiner*—Cathy Kingdon Worley
(74) *Attorney, Agent, or Firm*—McDonnell Boehnen Hulbert & Berghoff LLP (57) ABSTRACT

The invention provides methods and compositions for the production of transgenic plants, plant cells, embryos, and seeds that produce plants with floral organs that have increased mass and/or size as compared to wild-type plants. The transgenic plants can be transformed with a genetic construct comprising an ipt gene under the control of an APETAL3 promoter.

12 Claims, 5 Drawing Sheets

OTHER PUBLICATIONS

Gen Bank Accession No. X00639 dated Apr. 18, 2005.
Gen Bank Accession No. X00010 dated Sep. 12, 1993.
Gen Bank Accession No. M34934 dated Apr. 24, 1996.
Gen Bank Accession No. K02000 dated Mar. 13, 1996.
Gen Bank Accession No. AB062607 dated Feb. 14, 2004.
Gen Bank Accession No. AB061400 dated Jun. 2, 2001.
Gen Bank Accession No. AB062609 dated Feb. 14, 2004.
Gen Bank Accession No. AB062610 dated Feb. 14, 2004.
Gen Bank Accession No. AB061401 dated Jun. 2, 2001.
Gen Bank Accession No. AB062611 dated Feb. 14, 2004.
Gen Bank Accession No. AB061402 dated Jun. 2, 2001.
Gen Bank Accession No. AB062608 dated Feb. 14, 2004.
Gen Bank Accession No. AB061403 dated Jun. 2, 2001.
Gen Bank Accession No. AB062612 dated Feb. 14, 2004.
Gen Bank Accession No. AB061404 dated Jun. 2, 2001.
Gen Bank Accession No. AB062613 dated Feb. 14, 2004.
Gen Bank Accession No. AB061405 dated Jun. 2, 2001.
Gen Bank Accession No. AB062614 dated Feb. 14, 2004.
Gen Bank Accession No. AB061406 dated Jun. 2, 2001.
Gen Bank Accession NO. AAF0582 dated May 29, 2002.
Gen Bank Accession No. AAG52395 dated Jan. 19, 2001.
Gen Bank Accession No. CAB87756 dated Apr. 16, 2005.
Gen Bank Accession No. AAF00582 dated May 29, 2002.
Gen Bank Accession No. CAA22998 dated Apr. 16, 2005.
Gen Bank Accession No. AC068809 dated May 10, 2000.
Gen Bank Accession No. AAG50809 dated Jan. 19, 2001.
Gen Bank Accession No. BAB02782 dated Feb. 14, 2004.
Gen Bank Accession No. BAB02956 dated Feb. 14, 2004.
Koch, et al., "*Comparative Genomics and Regulatory Evolution: Conservation and Function of the Chs and Apetala3 Promoters*", *Mol. Bio. Evol.*, 18(10):1882-1891 (2001).
Kramer, et al., "*Molecular Evolution of Genes Controlling Petal and Stamen Development: Dupliction and Divergence Within the APETALA3 and PISTILLATA MADS-Box Gene Lineages*", *Genetics*, 149:765-783 (1998).
Hill, et al., "*Discrete spatial and temporal cis-acting elements regulate transcription of the Arabidopsis floral homeotic gene APETALA3*", *Development*, 125, 1711-1721 (1998).
Takei, et al., "Identification of Genes Encoding Adenylate Isopentenyltransferase, a Cytokinin Biosynthesis Enzyme, in Arabidopsis thaliana", *The Journal of Biological Chemistry*, vol. 276, No. 28, pp. 26405-26410 (2001).
Irish, et al., "Conservation of Floral Homeotic Gene Function between Arabidopsis and Antirrhinum", *The Plant Cell*, vol. 7, 1635-1644 (1995).

Krizek, et al., "*The Arabidopsis homeotic genes APETALA3 and PISTILLATA are sufficient to provide the B class organ identify function*", *Development* 122, 11-22 (1996).
Jack, et al., "The Homeotic Gene APETALA3 of Arabidopsis thaliana Encodes a MADS Box and Is Expressed in Petals and Stamens", *Cell*, vol. 68, 683-697 (1992).
Gan et al., "Inhibition of Leaf Senescence by Autoregulated Production of Cytokinin", *Science*, vol. 270, pp. 1986-1988 (1995).
Barry, et al., "*Identification of a cloned cytokinin biosynthetic gene*", *Proc. Natl. Acad. Sci. USA*, vol. 81, pp. 4776-4780 (1984).
Fang, et al., "Multiple cis Regulatory Elements for Maximal Expression of the Cauliflower Mosaic Virus 35S Promoter in Transgenic Plants", *The Plant Cell*, vol. 1, 141-150, 1989.
Odell, et al., "Identification of DNA sequences required for activity of the cauliflower mosaic virus 35S promoter", *Nature*, vol. 313, 810-12, 1985.
Irish, et al., "Conservation of Floral Homeotic Gene Function between Arabidopsis and Antirrhinum", *The Plant Cell*, vol. 7, 1635-1644, 1995.
Maiti, et al., "Promoter/leader deletion analysis and plant expression vectors with the figwort mosaic virus (FMV) full length transcript (FLt) promoter containing single or double enhancer domains", *Transgenic Research*, 6, 143-156 (1997).
Maiti, et al., "Isolation and Expression Analysis of Peanut Chlorotic Streak Caulimovirus (PCISV) Full-Length Transcript (FLt) Promoter in Transgenic Plants", *Biochemical and Biophysical Research Communications*, 244, 440-444 (1998).
Crespi, et al., "Fasciation induction by the phytopathogen Rhodococcus fascians depends upon a linear plasmid encoding a cytokinin synthase gene", *The EMBO Journal*, vol. 11, No. 3, pp. 795-804, 1992.
Goldberg, et al., "Nucleotide sequence of the tmr locus of Angrobacterium tumefaciens pTi T37 T-DNA", *Nucleic Acid Research*, vol. 12, No. 11, pp. 4665-4677 (1984).
Strabala, et al., "*Isolation and characterization of an ipt gene from the Ti plasmid Bo542*", *Mol. Gen. Genet.*, 216:388-394 (1989).
Carr, et al., "*Floral homeotic gene expression defines developmental arrest stages in Brassica oleracea L. vars. Botrytis and italica*", *Planta*, 201:179-188 (1997).
Heidekamp, et al., "Nucleotide sequence of the Agrobacterium tumefaciens octopine Ti plasmid-encoded tmr gene", *Nucleic Acids Research*, vol. 11, No. 18, 6211-6223 (1983).

\* cited by examiner

RB = right border
AP3 = apetal 3 promoter – approx 1800 bp
IPT = isopentenyl transferase gene – approx 700 bp
NOS = terminator
NPTII = kanamycin selectable marker
LB = left border

Figure 4

FLORAL ORGAN TISSUE-SPECIFIC EXPRESSION OF ISOPENTENYL TRANSFERASE

PRIORITY

This application claims the benefit of U.S. Ser. No. 60/540,984, filed Feb. 2, 2004, which is incorporated herein by reference in its entirety.

BACKGROUND OF THE INVENTION

Methods and compositions are needed in the ornamental plant industry, the vegetable production industry, and agronomic crops to increase to increase, inter alia, yield. By increasing yield of agronomic and fruit and vegetable crops, it would be possible to produce more food on less land, thus saving sustainable resources and labor costs and increasing profit margins for farmers. Methods and compositions are also needed in the ornamental plant industry to produce larger flowers allowing for increased amounts of color display and better sales.

SUMMARY OF THE INVENTION

One embodiment of the invention provides an isolated nucleic acid molecule comprising a nucleic acid molecule encoding isopentenyl transferase (IPT) operably linked to a nucleic acid molecule that comprises a promoter that drives tissue-specific expression in a floral ovary organ and at least one of the following floral organs: stigma, style, petal, sepal, receptacle or any combination thereof. The promoter can drive tissue-specific expression in all floral organs. The promoter that drives tissue-specific expression can be a promoter for APETALA3 (also referred to as AP3 herein).

Another embodiment of the invention provides an isolated nucleic acid molecule comprising a nucleic acid molecule encoding IPT operably linked to a nucleic acid molecule that comprises a promoter that drives tissue-specific expression in at least one of the following floral organs: stigma, style, petal, sepal, receptacle or a combination thereof, wherein the promoter does not drive tissue-specific expression in a floral ovary organ. The promoter that drives tissue-specific expression can be a promoter for APETALA3.

The isolated nucleic acid molecules of the invention can be present in a vector, a host cell, such as a plant cell, a transgenic plant, a transgenic seed, and/or a transgenic embryo.

Yet another embodiment of the invention provides a method for producing IPT in a host cell. The method comprises introducing a nucleic acid molecule encoding IPT operably linked to a nucleic acid molecule that comprises a promoter that drives tissue-specific expression in a floral ovary organ and at least one of the following floral organs: stigma, style, petal, sepal, receptacle or a combination thereof into the host cell and culturing the host cell under suitable conditions to express IPT. The host cell can be a plant cell.

Still another embodiment of the invention provides a method for producing IPT in a transgenic plant. The method comprises introducing a nucleic acid molecule encoding IPT operably linked to a nucleic acid molecule that comprises a promoter that drives tissue-specific expression in a floral ovary organ and at least one of the following floral organs: stigma, style, petal, sepal, receptacle or a combination thereof into a plant cell or plant tissue to form a transformed plant cell or transformed plant tissue. The transgenic plant is regenerated from the transformed plant cell or transformed plant tissue. The transgenic plant is grown under suitable conditions to express IPT.

Even another embodiment of the invention provides a method of producing a transgenic plant having increased mass or size or both of a floral ovary organ and at least one of the following floral organs: stigma, style, petal, sepal, receptacle or a combination thereof as compared to a wild-type plant. The method comprises introducing into a plant cell or plant tissue a nucleic acid molecule encoding IPT operably linked to a nucleic acid molecule that comprises a promoter that drives tissue-specific expression in a floral ovary organ and at least one of the following floral organs: stigma, style, petal, sepal, receptacle or a combination thereof to produce a transformed plant cell or a transformed plant tissue. A transgenic plant is regenerated from the transformed plant cell or transformed plant tissue. The promoter can drive tissue-specific expression in all floral organs.

Another embodiment of the invention provides a method of producing a transgenic plant having increased mass or size or both of at least one of the following floral organs: stigma, style, petal, sepal, receptacle or a combination thereof as compared to a wild-type plant, comprising introducing into a plant cell or plant tissue a nucleic acid molecule encoding IPT operably linked to a nucleic acid molecule that comprises a promoter that drives tissue-specific expression in at least one of the following floral organs: stigma, style, petal, sepal, receptacle or a combination thereof, wherein the promoter does not drive tissue-specific expression in a floral ovary organ, to produce a transformed plant cell or a transformed plant tissue. A transgenic plant is regenerated from the transformed plant cell or transformed plant tissue.

Another embodiment of the invention provides a method of making a transgenic plant that produces fruit or seeds or both that have increased mass or size or both as compared to a wild-type plant. The method comprises introducing into a plant cell or plant tissue an isolated nucleic acid molecule of the invention to produce a transformed plant cell or a transformed plant tissue; and regenerating a transgenic plant from the transformed plant cell or transformed plant tissue.

The instant invention provides compositions and methods that provide for large increases in the size of floral organs. Overall mass of floral organs in transgenic plant lines are also markedly increased. The methods and compositions of the invention provide significant opportunities in the ornamental plant industry, the vegetable production industry, and agronomic crops. By increasing yield of agronomic and fruit and vegetable crops, it is possible to produce more food on less land, thus saving sustainable resources and labor costs and increasing profit margins for farmers. By using this technology in ornamental flowering plants, larger flowers can be produced, allowing for increased amounts of color display and better sales, and the introduction of new flowering species to the market with larger flowers than previously observed. Use of this technology could significantly increase the overall yield of all of these crops by 20-50%, making the impact of this technology on harvestable yield unprecedented.

DETAILED DESCRIPTION OF THE INVENTION

A. Polynucleotides

The term "isolated nucleic acid molecule" is used to refer to a nucleic acid molecule that (1) has been separated from at least about 50%, 75%, 90%, or more of proteins, lipids, carbohydrates, or other materials with which it is naturally found when total nucleic acid is isolated from source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecules or other contaminants that are found in its natural environment that would interfere with, for example, its use in polypeptide production.

The term "nucleic acid sequence" or "nucleic acid molecule" is used to refer to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A recombinant nucleic acid is one that has a sequence that is not naturally occurring or has a sequence that is made by an artificial combination of two otherwise separated segments of sequence. Such artificial conditions can be achieved using genetic engineering techniques.

The recombinant nucleic acid molecules of the invention can readily be obtained in a variety of ways including, without limitation, chemical synthesis, genomic library screening, expression library screening, or PCR amplification of genomic DNA. See e.g., Sambrook et al., *Molecular Cloning: A Laboratory Manual* (Cold Spring Harbor Laboratory Press, 1989); *Current Protocols in Molecular Biology* (Ausubel et al., eds., Green Publishers Inc. and Wiley and Sons 1994).

One method for obtaining the recombinant promoters and nucleic acid molecules of the invention is the polymerase chain reaction (PCR). In this method, genomic DNA isolated from plant tissue is used as a template for PCR amplification. Two primers, typically complementary to two separate regions of a particular nucleic acid sequence, are then added to the nucleic acid sequence along with a polymerase such as Taq polymerase, and the polymerase amplifies the region of the nucleic acid sequence between the two primers.

Another method for obtaining the recombinant promoters and nucleic acid molecules of the invention is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. One method for such chemical synthesis is polymer-supported synthesis using standard phosphoramidite chemistry. Typically, the desired nucleic acid molecule will be several hundred nucleotides in length. Nucleic acids larger than about 100 nucleotides can be synthesized as several fragments using these methods. The fragments can then be ligated together to form the full-length nucleotide sequence. Other methods known to the skilled artisan can be used as well.

The term "identity," as known in the art, is used to refer to a relationship between two or more nucleic acid molecules or polypeptide molecules, as determined by comparing the sequences. In the art, "identity" also means the degree of sequence relatedness between nucleic acid molecules or polypeptide molecules, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "transgene," as used herein, refers to a chimeric nucleic acid molecule comprising an isolated promoter molecule and an isolated nucleic acid molecule operably linked to the promoter, wherein the chimeric nucleic acid molecule is capable of being expressed in a host cell. In one embodiment, the transgenes of the invention comprise a promoter, for example, an APETALA3 promoter, operably linked to a nucleic acid molecule encoding isopentenyl transferase (IPT).

The term "operably linked" is used to refer to an arrangement of flanking sequences wherein the flanking sequences so described are configured or assembled so as to perform their usual function. Thus, a flanking sequence operably linked to a coding sequence can be capable of effecting the replication, transcription, or translation of the coding sequence. For example, a coding sequence is operably linked to a promoter when the promoter directs transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

B. Promoters

The term "recombinant promoter" or "promoter," as used herein, means a nucleic acid molecule, operably linked to a coding sequence, that directs transcription of the coding sequence into mRNA. A promoter typically comprises a recognition site capable of directing RNA polymerase to initiate RNA synthesis at an appropriate transcription initiation site. A promoter can additionally comprise other sequences such as upstream promoter elements that can influence transcription initiation rate.

The term "tissue-specific expression," as it relates to promoter activity, refers to the ability of a promoter to drive the expression of an isolated nucleic acid molecule in less than all of the tissues of an organism into which the promoter and nucleic acid molecule are introduced. The term "constitutive expression," as it relates to promoter activity, refers to the ability of a promoter to drive the expression of an isolated nucleic acid molecule in substantially all of the tissues of an organism into which the promoter and nucleic acid molecule are introduced. In one embodiment, promoters of the invention provide tissue-specific expression and drive expression of an isolated nucleic acid molecule in floral organs of a plant.

A transgene of the invention is expressed in a plant in one or more floral organs of the plant. The transgene of the invention is not expressed or is expressed at very low levels in non-floral organs compared to the expression in one or more floral organs. Floral organs include stigma, style, petal, sepal, receptacle, and ovary. Fruit is a ripened ovary and is included in the definition of ovary. Fruit normally develops after fertilization. The ovules form seeds and the ovary wall forms the fruit wall (pericarp). "All floral organs" means stigma, style, petal, sepal, receptacle, and ovary.

The promoters drive tissue-specific expression of a nucleic acid molecule such that the level of the resulting mRNA in floral organs is expressed at a level that is about 5 fold, 10 fold, 100 fold, 1,000 fold, or more higher than expression in a wild-type plant. The level of mRNA can be measured either at a single time point or at multiple time points and as such the increase in mRNA can be an average increase or an extrapolated value derived from experimentally measured values. In one embodiment of the invention a promoter drives tissue-specific expression in a floral ovary organ and at least one of the following floral organs: stigma, style, petal, sepal, receptacle or a combination thereof. In another embodiment of the invention, a promoter drives tissue-specific expression in all floral organs. In yet another embodiment of the invention a promoter drives expression in at least one of the following floral organs: stigma, style, petal, sepal, receptacle or a combination thereof, but not in the floral ovary.

In one embodiment of the invention, the promoter comprises a promoter for the APETALA3 gene. APETALA3 is a MADS regulatory gene responsible for floral organ identity. A promoter can be derived from any flowering plant, including monocotyledons and dicotyledons. In one embodiment the promoter is derived from *Aethionema grandiflora, Arabidopsis griffithiana, A. thaliana, A. alpine, Arabis drummondii, Arabis glabra, Arabis jaquinii, Arabis turrita, Barbarea vulgaris, Brassica oleracea* (see e.g., Carr & Irish, Planta, 201:179-188 (1997)), *Capsella reubella, Cardamine amara, Cardaminopsis petraea, Cardaminopsis halleri, Cochlearia excelsa, Cochlearia, Fourraea alpine, Lepidium campestre, Rorippa amphibian, Sinapis alba*. In one embodiment of the invention, the promoter is disclosed in GenBank Accession No.: AL132971, U30729, AF248971, AF248972 AF248984, AF248981, AF248973, AF248974 AF248975, AF248982, AF248978, AF043610, AF248980, AF248983, AF248985, AF248970, AF248979, AF248976, AF248977, AF248968, AF248969, ATU30729, and AF043610.

One embodiment of the invention provides a minimal promoter. A minimal promoter is also a promoter of the invention. A minimal promoter will typically comprise a TATA box and transcriptional start sequence, but will not contain additional stimulatory and repressive elements. The boundaries defining the minimal promoter sequence can be ambiguous. That is, the nucleotide positions defining the 5' and 3' ends of a minimal promoter can vary slightly depending on, for example, the expression-reporter system used. The boundaries defining the minimal promoter can be determined using known techniques, described in, for example, Fang et al., (1989) Plant Cell 1:141-50 and Odell et al., (1985) Nature 313:810-2. A minimal promoter directs tissue-specific expression in one or more floral organs.

The *Arabidopsis* APETALA3 promoter has been studied in detail by Hill et al., Development (1998) 125:1711. Hill et al. determined that of the 1.7 kb *Arabidopsis* APETALA3 promoter sequences from about −727 to about +1 were sufficient to confer all normal aspects of the normal APETALA3 expression. Within this region, the proximal early element (from about −224 to about 83) and the distal early element (from about −727 to about 615) are two discrete cis-acting elements. Cis-acting elements required for petal-specific expression are located at about 224 to about −83. A fragment of the APETALA3 promoter from about −328 to about +1 is sufficient to confer petal-specific expression in *Arabidopsis*. The distal stamen element (about −556 to about −374) and the proximal stamen element (about −328 to about −83) are required for stamen-specific expression. Sequences from about −374 to about −328 are not required to mediate expression. Sequences from about −224 to about −83 are required for early expression (stages 3–5) and for petal-specific expression during floral development. Three CaRG boxes are present at about −95 to about −104, about −168 to about −177, and about −120 to about −129.

Several genes may be required for APETALA3 expression in *Arabidopsis*, e.g., AP1, UFO, LFY, AP3, PI, SUP and/or combinations thereof. These genes are present in the plants or host cells of the invention or can be supplied to the plant or host cell using genetic engineering techniques well-known to those of skill in the art.

An isolated promoter sequence of the instant invention can be modified to provide for a range of expression levels of the coding sequence. Less than the entire promoter region can be used and the ability to drive tissue-specific expression retained. Expression levels of mRNA can be decreased with deletions of portions of the promoter sequence. Thus, the promoter can be modified to be a weak or strong promoter. A weak promoter drives expression of a coding sequence at a low level. A strong promoter drives expression of a coding sequence at a high level.

Fragments or portions of a promoter nucleotide sequence disclosed herein are also encompassed by this invention. For example, fragments of an *Arabidopsis*, such as *A. thaliana*, APETALA3 promoter are promoter fragments of the invention. Fragments of promoters are capable of driving tissue-specific expression in floral organs. The portions of an APETALA3 promoter present in a fragment vary depending upon in which floral organs expression is desired. Hill et al. (Development, 125:1711-1721 (1998)) and Koch et al. (Mol. Biol. Evol. 18:1882-1891 (2001)) provide guidance as to which portions should be retained. Such fragments will comprise at least about 20, 50, 75, 100, 150, 200, 300, 400, 500, 750, 1,000, 1,250, or 1,700 contiguous nucleotides of the promoter nucleotide sequences disclosed herein. In one embodiment of the invention an APETALA3 promoter comprises one or more of three CArG box motifs as described by Koch et al., supra. In one embodiment of the invention an APETAL3 promoter comprises three CArG box motifs as disclosed in Hill et al. and/or Koch et al. In one embodiment of the invention an APETAL3 promoter comprises one or more of the conserved regions designated as region 1, region 2, region 3a, region 3b, and region 4 in Koch et al. In one embodiment of the invention an APETALA3 promoter comprises an MYB-homolog-binding site at position 78 (as designated by Koch et al.), a region for circadian expression overlapping this myb element (as designated by Koch et al.), a G-box-like CACCTG motif overlapping this myb element (as designated by Koch et al.), core sites (AAAG) at positions 73 and 243 (as designated by Koch et al.), an ACTTTA motif at positions 53 and 421 (as designated by Koch et al.). An APETALA3 promoter of the invention can comprise 1, 2, 3, 4, 5, 6, 7, 8, 9, 10, 11, 12, 13, 14, or 15 regions selected from: the first, second, or third CArG boxes, region 1, region 2, region 3a, region 3b, region 4, MYB-homolog-binding site, a region for circadian expression, a G-box-like CACCTG motif, core site (AAAG), and an ACTTTA motif (as designated by Hill et al. or Koch et al.) or combinations and duplications thereof. These regions can have the sequences as disclosed in Hill et al. or Koch et al., or can have sequences with 75%, 85%, 90%, 95%, 98%, or 99% sequence identity to those sequences in Hill et al. or Koch et al., wherein one of skill in the art would recognize that the sequences were analogous to the elements and regions described by Hill et al. and Koch et al.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, WI 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Such fragments can be obtained by use of restriction enzymes to cleave the naturally-occurring promoter nucleotide sequences disclosed herein; by synthesizing a nucleotide sequence; through the use of, e.g., PCR technology. See e.g., Mullis et al. (1987) Methods Enzymol. 155:335-350, and Erlich, ed. (1989) PCR Technology (Stockton Press, New York). Fragments of promoter sequences are capable of driving tissue-specific expression and are useful as probes to identify similar sequences.

Promoter activity can be measured by, for example, RNA gel blot analysis and reporter activity measurements when using transcriptional fusions. See, for example, Sambrook et al. (1989) Molecular Cloning: A Laboratory Manual (2nd ed. Cold Spring Harbor Laboratory, Cold Spring Harbor, N.Y.). The activity or strength of a promoter can be measured by the amount of mRNA it produces or by the amount of protein accumulation in a cell or tissue relative to a promoter whose transcriptional activity is known. The activity or strength of a promoter can be expressed relative to a well-characterized promoter. For example, a promoter can be operably linked to a reporter sequence (e.g., GUS) and introduced into a specific cell type. A known promoter can be similarly prepared and introduced into the same cell. Transcriptional activity of the promoter is then determined by comparing the amount of reported expression, relative to the known promoter. RT-PCR can also be used to determine the transcriptional activity of the promoter.

The invention also provides promoters wherein promoter sequences are duplicated. The duplication can provide enhanced promoter activity. For example, two or more copies of an enhancer element in tandem often results in increased expression levels. See e.g., U.S. Pat. No. 5,424,200; Maiti et al., (1997) Transgenic Res. 6:143-56; and Maiti & Shepard (1998) Biochem. Biophys. Res. Commun. 244:440-44.

Enhancers can be used in combination with a promoter of the invention. Enhancers are nucleotide sequences that increase expression. Enhancers are known in the art and include, for example, an SV40 enhancer region and a 35S enhancer element.

The invention also provides chimeric promoters comprising a portion of a promoter of the invention. For example, a chimeric promoter can comprise one or more promoter elements of the invention combined with one or more promoter elements derived from another promoter of the invention or any other promoter. The portion of a chimeric promoter that is not derived from a promoter of the invention can be derived from, for example, another plant promoter or a viral promoter, or from any other naturally occurring promoter. Alternatively, that portion can be synthetic or a modified variation or a naturally-occurring promoter.

C. Isopentenyl Transferase

Isopentenyl transferase (IPT) (which is also knows as tmr in *Agrobacterium tumefaciens*) functions in the biosynthesis of the cytokinin isopentenyladenosine. IPT catalyzes the condensation of isopentenyl pyrophosphate and adenosine monophosphate giving isopentenyl AMP. Isopentenyl AMP is the precursor of several other cytokinins. IPT gene sequences can be derived from, e.g., plants, yeast, and bacteria, including, for example, *Agrobacterium tumefaciens*.

Examples of IPT sequences are presented in: Crespi et al., EMBO J. 11:795-804 (1992); Goldberg et al., Nucleic Acids. Res. 12:4665-4677 (1984); Heide Kamp et al., Nucleic Acids Res., 11:6211-6223 (1983); Gan & Amasino, Science, 270:1986 (1995); Strabala et al., Mol. Gen. Genet. 216:388-394 (1989); Takei et al., J. Biol. Chem. 276:26405 (2001); GenBank Accession Numbers: NC003308, X14410, BQ698482, BM15885, BG275588, BF609263, BF169921, AF109376, BH012217, AB032122, AJ42867, AB025109, M91610, M15991, X00639, X00010, M34934, K02000, AAF00582, AF109376, AB062607, AB061400, AB062609, AB062610, AB061401, AB062611, AB061402, AB062608, AB061403, AB062612, A13061404, AB062613, AB061405, AB062614, AB061406, AAG52395, AAF00582, CAB87756, CAA22998, AC068809, AAG50809, BAB02782, and BAB02956.

Portion or fragments of a sequence encoding IPT can be used in the instant invention as long as the portion or fragment retains 75%, 80%, 90%, 95%, 100%, 110% or 120% of IPT biological activity. The biological activity of IPT can be assayed using methods that are well known in the art and described in, inter alia, Takei et al., J. Biol. Chem. 276:26405 (2001), Barry et al., Proc. Natl. Acad. Sci. USA, 81:4776-4780 (1984).

D. Vectors

The term "vector" is used to refer to any molecule (e.g., nucleic acid, plasmid, or virus) used to transfer one or more nucleic acids to a host cell. Vectors containing transgenes of the invention can be prepared by inserting a recombinant promoter and an isolated nucleic acid molecule into an appropriate vector using standard ligation techniques. Typically, vectors of the invention will also contain sequences (in addition to the transgene) for plasmid maintenance and for cloning and expression of exogenous nucleotide sequences. Such sequences, or "flanking sequences," typically include one or more of the following: one or more enhancer sequences, an origin of replication, a transcriptional termination sequence, a sequence encoding a leader sequence for polypeptide secretion, a polyadenylation sequence, a polylinker region for inserting the nucleic acid encoding the polypeptide to be expressed, and a selectable marker element. In preferred embodiments, a recombinant promoter and isolated nucleic acid molecule are introduced into a transformation vector such as, pHK, for example, that contains spectomycin resistance gene as a selectable marker for host bacteria and a kanamycin resistance gene as a selectable marker for a host plant.

Flanking sequences can be homologous (i.e., from the same species or strain as the host cell), heterologous (i.e., from a species other than the host cell species or strain), hybrid (i.e., a combination of flanking sequences from more than one source), or synthetic. As such, the source of a flanking sequence can be any prokaryotic or eukaryotic organism, any vertebrate or invertebrate organism, or any plant, provided that the flanking sequence is functional in, and can be activated by, the host cell machinery.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector.

A transcription termination sequence is typically located 3' of the end of a polypeptide coding region and serves to terminate transcription. While a transcription termination sequence is easily cloned from a library or even purchased commercially as part of a vector, it can also be readily synthesized using methods for nucleic acid synthesis such as those described herein. In one embodiment, vectors of the invention contain a nopaline synthase gene terminator sequence (NOS3') for terminating transcription of an isolated nucleic acid molecule operably linked to the recombinant promoter.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin; (b) complement auxotrophic deficiencies of the cell; or (c) supply critical nutrients not available from complex media. Selectable markers include, for example, kanamycin resistance, ampicillin resistance, and tetracycline resistance. Neomycin resistance can also be used for selection in prokaryotic and eukaryotic host cells.

Vectors of the invention can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

The vectors of the invention can be inserted into a suitable host cell for amplification or polypeptide expression. The transfection and transformation of vectors of the invention into a selected host cell can be accomplished by well known methods including transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

E. Host Cells The term "host cell," as used herein, refers to a cell that has been transformed, or that can be transformed with a nucleic acid sequence. The term includes the progeny of the parent cell, whether or not the progeny is identical in morphology or in genetic make-up to the original parent, so long as the selected nucleic acid is present.

The term "transfection," as used herein, refers to uptake of foreign or exogenous nucleic acid by a cell, and a cell has been "transfected" when the exogenous nucleic acid has been introduced inside the cell membrane. A number of transfection techniques are well known in the art. Such techniques can be used to introduce one or more exogenous nucleic acid moieties into suitable host cells.

The term "transformation" is used to refer to a change in a cell's genetic characteristics, and a cell has been transformed when it has been modified to contain a new nucleic acid. For example, a cell is transformed where it is genetically modified from its native state. Following transfection, for example, transforming nucleic acid can recombine with that of the cell by physically integrating into a chromosome of the cell, can be maintained transiently as an episomal element without being replicated, or can replicate independently as a plasmid. A cell is considered to have been stably transformed when the nucleic acid is replicated with the division of the cell.

The term "naturally occurring" or "native" when used in connection with biological materials such as nucleic acid molecules, polypeptides, host cells, and the like, refers to materials that are found in nature and are not manipulated by man. Similarly, "non-naturally occurring" or "non-native" as used herein refers to a material that is not found in nature or that has been structurally modified or synthesized by man.

Host cells can be prokaryotic host cells (such as E. coli), eukaryotic host cells (such as a yeast, insect, plant, or vertebrate cell). In one embodiment, the host cell is a plant cell. A number of suitable host cells are known in the art and many are available from the American Type Culture Collection (ATCC), Manassas, Va. Examples include, but are not limited to, seed plants, i.e., angiosperms (including monocotyledons and dicotyledons) and/or gymnosperms. Examples of seed plants include cereal plants, leguminous plants, oilseed plants, hardwood trees, fruit-bearing plants and ornamental flowers. Examples of plants in these non-exclusive categories include, for example, soybean, peanut, *Phaseolus vulgaris* (e.g., kidney beans, black beans, white beans), *Vicia faba, Pisum sativum, Cicer aeietinum, Lens culinaris*, oil seed rape, sunflower, linseed, cotton, coffee, corn, rice, wheat, barley, oats, orchard grass, guinea grass, sorghum, turfgrass, and other cereals, nuts, legumes, tomatoes, citrus fruit such as orange trees, grapefruit trees, lemon trees and lime trees, grapes, hops, apples, pears, peaches, plums, cherries, bananas, blackberries, blueberries, raspberries, strawberries, pineapples, dates, avocadoes, olives, coconuts, cucumbers, eggplants, *Petunia* (*Petunia hybrida*), Carnation (*Dianthus caryophyllus*), Cyclamen (*Cyclamen* spp.), *Delphinium* (*Delphinium* spp.), Geranium (*Pelargonium* & *Geranium* spp.), Sweet pea (*Lathyrus odoratus*), Snapdragon (*Antirrhinum majus*), Begonia (*Begonia sp.*), Rose (*Rosa* spp.), orchid, lily, tulip, *chrysanthemum, camellia*. Gymnosperm seed plants include, for example, cycads, ginkgo, conifers and gnetophytes. Candidate cells can be genotypically deficient in a selectable marker gene, or can contain a dominantly acting selectable marker gene.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like can also be employed in this method.

Host cells comprising transgenes or vectors of the invention can be cultured using standard media well known to the skilled artisan. The media will usually contain all nutrients necessary for the growth and survival of the cells. Typically, an antibiotic or other compound useful for selective growth of transfected or transformed cells is added as a supplement to the media. The compound to be used will be dictated by the selectable marker element present on the vector with which the host cell was transformed. For example, where the selectable marker element is kanamycin resistance, the compound added to the culture medium will be kanamycin. Other compounds for selective growth include ampicillin, tetracycline, and neomycin.

Transfection and transformation methods for host cells, and in particular, plant host cells are well known in the art. For example, *Agrobacterium*-mediated transformation of plant cells is well known. See e.g., Glick and Thompson (eds.) Methods in Plant Molecular Biology and Biotechnology, Boca Raton, FL, CRC Press (1993); Wang et al., (ed.), Transformation of Plants and Soil Microorganisms, Cambridge, UK: University Press (1995); Biochemistry & Molecular Biology Of Plants, Buchanan et al. (eds), John Wiley & Sons CITY (2002); Plants, Genes, and Crop Biotechnology, Chrispeels et al., Jones and Bartlett (CITY), 2$^{nd}$ Ed., (2002); U.S. Pat. Nos. 6,603,061, 6,483,013, 6,455, 761, 6,384,301, 6,369,298, 6,274,791, 6,037,522, 5,981,840, 5,792,935, 5,563,055, 5,376,543, 5,169,770, 6,521,458, 6,265,638.

Transformation of host cells can also be accomplished using microprojectile-mediated delivery (i.e., particle bombardment). See e.g., Klein et al., Nature, 327:70-73 (1987); Duan et al., Nature Biotech., 14:494-498 (1996); Shimamoto, Curr. Opin. Biotech, 5:158-162 (1994). U.S. Pat. Nos. 5,932,782, 6,297,056, 6,570,067, 6,258,999. Microparticles can be coated with a transgene of the invention and accelerated at high speed into, for example, host cells or plant tissue using a device such as a BIOLISTIC™ PDS-1000, HELIOS™ Gene Gun (Bio-Rad, Hercules, Calif.).

Transformation of plant protoplasts can be accomplished as described in, for example, Hiei et al., The Plant J. 6(2):271-282 (1994); Shiimamoto, Science, 270:1772-1773 (1995), U.S. Pat. Nos. 5,508,184, 5,770,450, 4,940,839, 5,350,689.

Electroporation of cultured plant explants can be accomplished as described in, for example, U.S. Application Pub. No. 20030115641.

The amount of IPT produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, or activity assays such as DNA binding gel shift assays.

In one embodiment, IPT is produced in a transgenic plant by introducing a transgene comprising a recombinant promoter and an isolated nucleic acid molecule encoding IPT, wherein the nucleic acid molecule is operably linked to the promoter, into a plant cell or tissue; regenerating a transgenic plant from the transformed plant cell or transformed plant tissue; and then growing the transgenic plant under suitable conditions to express the protein. In one embodiment, a vector comprising the transgene is introduced into a plant cell or tissue using *Agrobacterium*mediated transformation. The transformation vectors are transferred to *Agrobacterium*through triparental mating. Plant tissue is transformed with this construct through *Agrobacterium*mediated transformation. Transformants are selected on tissue culture media containing appropriate antibiotics. In another embodiment, the transgenic plants thus obtained have floral organs with greater mass or size or both as compared to a wild-type plant.

F. Transgenic Plants

The invention also provides methods for producing transgenic plants, transgenic plant cells, transgenic embryos, and transgenic seeds comprising a promoter of the invention operably linked to an IPT nucleic acid sequence. A suitable plant cell is selected and transformed with a recombinant vector or a transgene of the invention. The transformed host cell is cultured under conditions effective to produce a plant.

The regeneration, development, and cultivation of plants from transformed plant protoplast or explants is well know in the art. See e.g., Dodds & Roberts, Experiments in Plant Tissue Culture, 1995, Cambridge University Press, New York; Davey (ed.), *Agrobacterium*Protocols, 1995, Humana Press, New Jersey; Smith, Plant Tissue Culture, 2000, Academic Press, New York. For example, transformants are generally cultured in the presence of a selective media that selects for successfully transformed cells and induces the regeneration of plant shoots. The shoots are transferred to an appropriate root-inducing medium containing a selective agent and an antibiotic to prevent bacterial growth. Shoots that develop roots are transplanted to soil or other media to allow the continued development of roots.

Methods for producing IPT in a host cell, such as a plant host cell, can comprise introducing a transgene of the invention into the host cell and culturing the host cell under suitable conditions to express IPT.

Methods for producing IPT in a transgenic plant can comprise, for example, introducing a transgene of the invention into a plant cell or plant tissue to form a transformed plant cell or transformed plant tissue, regenerating a transgenic plant from the transformed plant cell or transformed plant tissue, and growing the transgenic plant under suitable conditions to express IPT.

Transgenic plants having increased mass of a floral ovary organ and at least one of the following floral organs: stigma, style, petal, sepal, receptacle or a combination thereof as compared to a wild-type plant can be produced by methods of the invention. Such methods can comprise introducing into a plant cell or plant tissue the isolated nucleic acid molecule comprising a nucleic acid molecule encoding IPT operably linked to a nucleic acid molecule that comprises a promoter that drives tissue-specific expression in a floral ovary organ and at least one of the following floral organs: stigma, style, petal, sepal, receptacle or a combination thereof to produce a transformed plant cell or a transformed plant tissue. The transgenic plant is regenerated from the transformed plant cell or transformed plant tissue.

Transgenic plants have increased mass or size or both of a floral ovary organ and at least one of the following floral organs: stigma, style, petal, sepal, receptacle or a combination thereof as compared to a wild-type plant or having increased mass or size or both of all floral organs as compared to a wild-type plant can be produced by, for example, introducing into a plant cell or plant tissue an isolated nucleic acid molecule comprising a nucleic acid molecule encoding IPT operably linked to a nucleic acid molecule that comprises a promoter that drives tissue-specific expression in the desired floral organs to produce a transformed plant cell or a transformed plant tissue. The transgenic plant is regenerated from the transformed plant cell or transformed plant tissue.

A transgenic plant having increased mass or size or both of at least one of the following floral organs: stigma, style, petal, sepal, receptacle or a combination thereof (but not a floral ovary organ) as compared to a wild-type plant can be produced by, for example, introducing into a plant cell or plant tissue an isolated nucleic acid molecule comprising a nucleic acid molecule encoding IPT operably linked to a nucleic acid molecule that comprises a promoter that drives tissue-specific expression in the desired floral organ tissues to produce a transformed plant cell or a transformed plant tissue. A transgenic plant is regenerated from the transformed plant cell or transformed plant tissue.

A transgenic plant that produces fruit or seeds or both that have increased mass or size or both as compared to a wild-type plant, can be produced by, for example, introducing into a plant cell or plant tissue an isolated nucleic acid molecule comprising a nucleic acid molecule encoding IPT operably linked to a nucleic acid molecule that comprises a promoter that drives tissue-specific expression in floral organ tissues to produce a transformed plant cell or a transformed plant tissue. A transgenic plant is regenerated from the transformed plant cell or transformed plant tissue and transgenic fruits or transgenic seeds or both are collected from the plant.

The location of expression of IPT in transgenic plants of the invention can vary depending upon where a nucleic acid molecule of the invention integrates into a plant genome. For example, IPT can be produced in one or more floral organs, including a combination of floral organs, including fruit and seeds. One of skill in the art can easily determine in which floral organs IPT is expressed using, for example, assays described in Takei et al., J. Biol. Chem. 276:26405 (2001), Barry et al., Proc. Natl. Acad. Sci. USA, 81:4776-4780 (1984). Genomic analysis of a transgenic plant can also be done to determine were in the genome a nucleic acid molecule of the invention has inserted. Analysis of segregation of the transgene in progeny of transgenic plants of the invention can be done to demonstrate stable inheritance of transgenes.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings, as stated in the MPEP. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group. The examples, which follow, are illustrative of specific embodiments of the invention, and various uses thereof. They are set forth for explanatory purposes only, and are not to be taken as limiting the invention.

EXAMPLE

Figure 4:
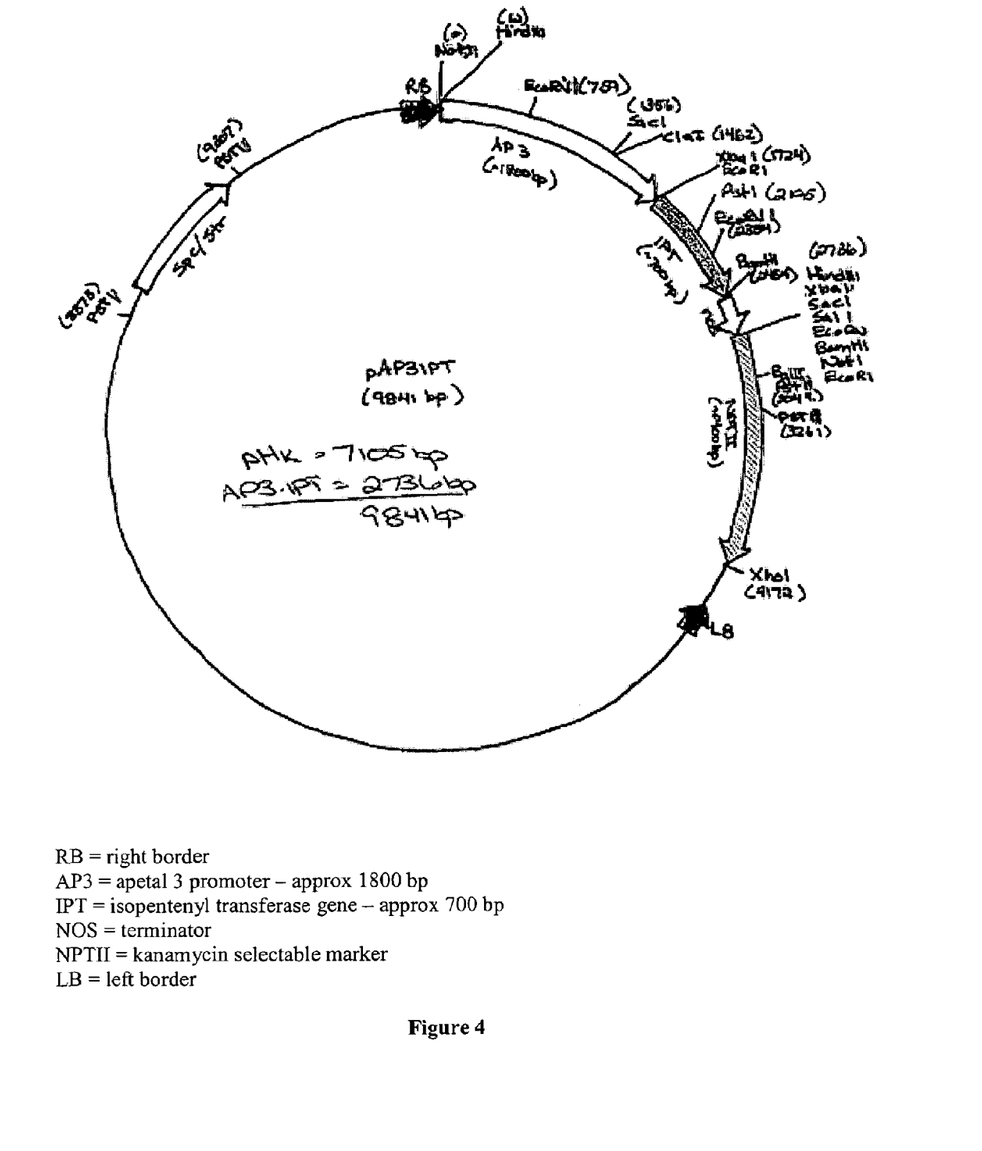
FIG. 4 shows a diagram of the pAP3IPT plasmid.

A gene encoding isopentenyl transferase was fused with a gene promoter that can drive expression of genes in all floral organs (APETALA3). For production of transgenic plants with flower specific overexpression of IPT a 700 bp segment of the IPT cDNA was cloned into a vector downstream from 1800 bp of the AP3 promoter and upstream of the *Agrobacterium* nopaline synthase (nos) terminus region in the sense orientation (FIG. 4). This construct was then cloned into a transformation vector containing a gene for kanamycin resistance (NPTII) within the transgene. The transformation vector was transferred to *Agrobacterium* through triparental mating. Petunia plants (cv. Mitchell Diploid) were transformed with these constructs according the methods of Jorgensen et al. (1996) to create plants that produce increased levels of cytokinins in floral tissues of plants (stamens, pistils, petals, sepals fruits and seeds). Increased expression of the AP3-IPT construct in transgenic petunia plants led to the production of altered flower morphologies. In particular, increased mass of all floral organs, including increases in fruit and seed weight was observed.

Figure 1:
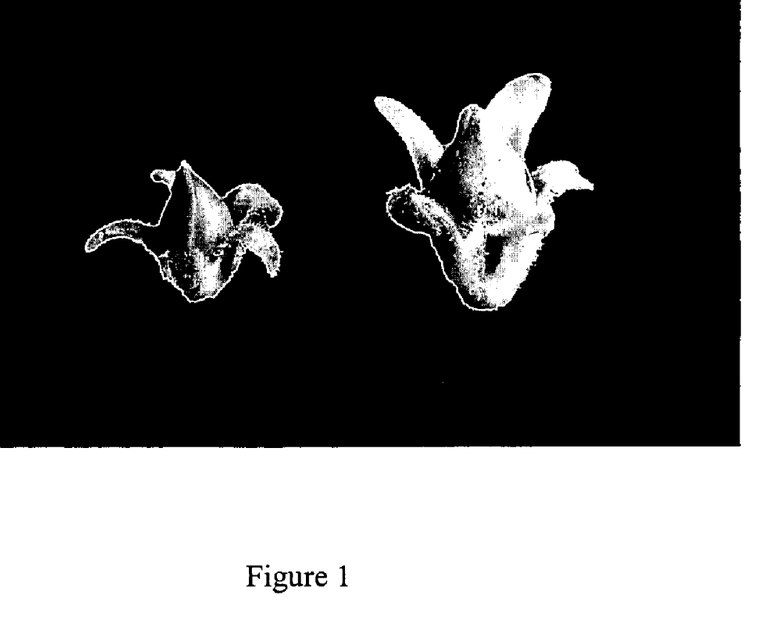
FIG. 1 shows excised fruit (ovary) produced on Wild-type Petunia hybrida 'Mitchell Diploid' plants (left) and transgenic T1 generation AP3-IPT plants (right) approximately 20 days after pollination.

FIG. 1 shows excised fruit (ovary) produced on Wild-type Petunia hybrida 'Mitchell Diploid' plants (left) and transgenic T1 generation AP3-IPT plants (right) approximately 20 days after pollination.

Figure 2:
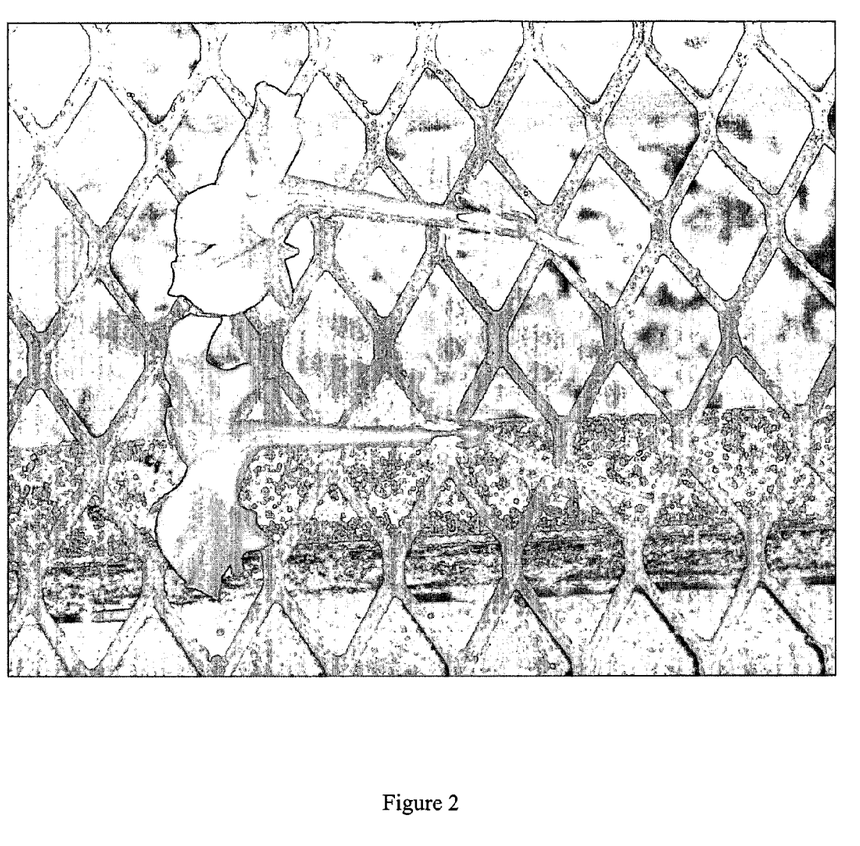
FIG. 2 shows excised flowers produced on wild-type Petunia hybrida 'Mitchell Diploid' plants (bottom) and transgenic T1 generation AP3-IPT plants (top).

FIG. 2 shows excised flowers produced on wild-type Petunia hybrida 'Mitchell Diploid' plants (bottom) and transgenic T1 generation AP3-IPT plants (top).

Figure 3:
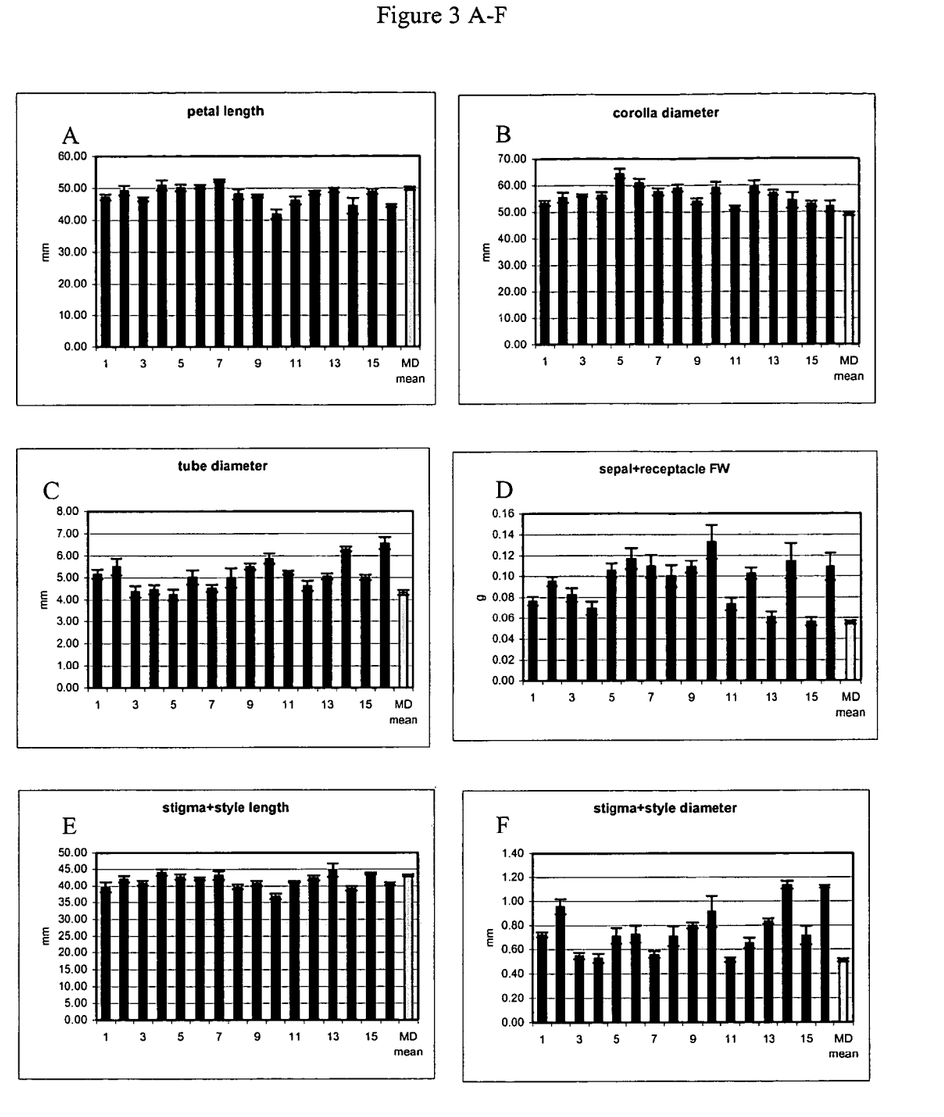
FIG. 3 shows quantification of floral size of 3 flowers/plant collected from wild-type Petunia hybrida 'Mitchell Diploid' plants (light bars) and 16 segregating T1 progeny from transgenic AP3-IPT plants (dark bars). Panel A shows petal length; Panel B shows corolla diameter; Panel C shows tube diameter; Panel D shows sepal+receptacle FW; Panel E shows stigma+style length; Panel F shows stigma+style diameter; Panel G whole flower FW; Panel H shows petal FW; Panel I shows ovary FW; Panel J shows stigma+style FW; Panel K shows ovary length; Panel L shows ovary diameter.

FIG. 3 shows quantification of floral size of 3 flowers/plant collected from wild-type Petunia hybrida 'Mitchell Diploid' plants (clear bars) and 16 segregating T1 progeny from transgenic AP3-IPT plants (dark bars). Panel A shows petal length; Panel B shows corolla diameter; Panel C shows tube diameter; Panel D shows sepal+receptacle FW; Panel E shows stigma+style length; Panel F shows stigma+style diameter; Panel G whole flower FW; Panel H shows petal FW; Panel I shows ovary FW; Panel J shows stigma+style FW; Panel K shows ovary length; Panel L shows ovary diameter.

We claim:

1. An isolated nucleic acid molecule comprising a polynucleotide molecule encoding isopentenyl transferase (IPT) operably linked to a polynucleotide molecule that comprises a APETALA3 promoter that drives tissue-specific expression in a floral organ; wherein a plant comprising said nucleic acid molecule produces flowers that have an increase in the size of the corolla, tube, stigma, style, and ovary; and an increase in mass of the sepal and receptacle, whole flower, petal, ovary, stigma, and style compared to flowers produced by a control plant of the same genetic background.

2. The isolated nucleic acid molecule of claim 1, wherein the nucleic acid molecule comprises a APETALA3 promoter that drives tissue-specific expression in all floral organs.

3. A vector comprising the isolated nucleic acid molecule of claim 1.

4. A host cell comprising the isolated nucleic acid molecule of claim 1.

5. The host cell of claim 4, wherein the host cell is a plant cell.

6. A transgenic plant comprising the isolated nucleic acid molecule of claim 1.

7. A transgenic seed or a transgenic embryo comprising the isolated nucleic acid molecule of claim 1.

8. A method for producing IPT in a transgenic plant comprising:
    (a) introducing the nucleic acid of claim 1 into a plant cell or plant tissue to form a transformed plant cell or transformed plant tissue;
    (b) regenerating a transgenic plant from the transformed plant cell or transformed plant tissue;
    (c) growing the transgenic plant under suitable conditions to express IPT.

9. A method of producing a transgenic plant having flowers exhibiting an increase in the size of the corolla, tube, stigma, style, and ovary; and an increase in mass of the sepal and receptacle, whole flower, petal, ovary, stigma, and style compared to flowers from a control plant of the same genetic background; said method comprising introducing into a plant cell or plant tissue the nucleic acid molecule of claim 1 to produce a transformed plant cell or a transformed plant tissue; and regenerating a transgenic plant from the transformed plant cell or transformed plant tissue.

10. The method of claim 9, wherein the nucleic acid molecule comprises an APETALA3 promoter that drives tissue-specific expression in all floral organs.

11. A transgenic plant produced by the method of claim 9.

12. A transgenic fruit comprising the isolated nucleic acid of claim 1.

* * * * *